United States Patent [19]

Sagen

[11] Patent Number: 5,762,925
[45] Date of Patent: Jun. 9, 1998

[54] PREVENTING OPIATE TOLERANCE BY CELLULAR IMPLANTATION

[76] Inventor: Jacqueline Sagen, 2509 W. Farwell, Chicago, Ill. 60645

[21] Appl. No.: 334,187

[22] Filed: Nov. 3, 1994

[51] Int. Cl.⁶ .................. A61K 35/55; C12N 5/06
[52] U.S. Cl. .................. 424/93.7; 604/49; 435/240.2; 424/563
[58] Field of Search ............... 424/93.7, 563; 604/49; 435/240.2

[56] References Cited

U.S. PATENT DOCUMENTS 4,753,635  6/1988  Sagen ........................... 604/49
4,980,174  12/1990  Sagen ........................... 424/563
5,550,050  8/1996  Holland et al. ................ 435/240.2

OTHER PUBLICATIONS

Guststein et al., Brain Research 680(1–2): 173–179 (1995).

Miglecz et al., Psychopharmacology 62(1): 29–34 (Mar. 29, 1979).

*Primary Examiner*—Jean C. Witz

[57] ABSTRACT

The use of CNS transplants, in particular adrenal medullary transplants, in reducing and/or preventing tolerance to opiates.

4 Claims, 2 Drawing Sheets

PREVENTING OPIATE TOLERANCE BY CELLULAR IMPLANTATION

BACKGROUND OF THE INVENTION

1. Technical Field

The present invention relates to a method for reducing the development of tolerance to opiates, and thereby inhibiting the development of tolerance to and dependence on opiates, without substantial alteration of their analgesic effects.

2. Description of the Prior Art

The management of chronic pain is one of the greatest challenges in modern medicine. Millions of people suffer from chronic pain due to a variety of causes such as arthritis, cancer and nerve injury. For centuries, opiates have been used to treat pain. The prototype of the analgesia-producing opiates is morphine. Morphine is a rapid and effective treatment for pain, but its long term use is limited due to negative side effects. Unfortunately, the most serious of these side effects, the development of tolerance and dependence, are the hardest to counteract. Recent research in the areas of drug addiction and tolerance, however, has indicated that tolerance, dependence and analgesia may be modulated by different neurochemical systems and/or different receptor subtypes.

To date, a number of substances which will reduce the development of opiate tolerance have been found. U.S. Pat. No. 5,057,519 to Suberg discloses a series of benzaminde-type $5HT_3$ antagonists such as zacopride, batanopride and BMY 33462 which act to reduce the development of opiate tolerance. In addition, Trujilo and Akil have shown that non-competitive NMDA antagonists such as MK-801, ketamine, dextrophan and phencyclidine are capable of reducing opiate tolerance as well (1994, Brain Res. 633(1–2):178–88). Finally, Bhargava discusses the effect of NG-monomethyl-L-arginine (NMMA), an inhibitor of nitric oxide synthase, on the development of tolerance to kappa-opiate agonists (1994, Pharmacology 48(4):233–41).

One of the more recent advances in treating chronic pain is by implantation of cellular material which release analgesic substances directly into the central nervous system (CNS). The effectiveness of this technique has already been demonstrated in humans (Winnie et al, 1993, Anesthesiology, 79(4):644–53; Aebischer et al, 1994, Cell Transplant. 3(3):229). It has been further suggested that engineered cell lines might be ideal for this purpose. While cell lines such as AtT-20, AtT-20/hENK and B16 F1C29 can produce antinociception, the implantation of each of these cell lines has also resulted in the development of tolerance to selected analgesic substances (Wu et al, J. Neurosci 14(8):4806–14; Wu et al, Pain 56(2):203–10). Thus, it would be desirable to have a cell type which could be co-grafted and would reduce the development of tolerance.

The adrenal medulla is composed of chromaffin cells supported by connective tissue elements and profusely supplied by nerves and blood vessels. Ganglion cells are present but are usually difficult to find in routine sections. Chromaffin cells are derived from neuroectoderm and generally release catecholamines (epinephrine and norepinephrine). Furthermore, chromaffin cells have been shown to release a variety of other neuroactive substances as well. In fact, Unsicker described the release of substances from chromaffin cells as a "trophic cocktail" (Unsicker, 1993, Exp. Neuro. 123:167–73). As a result, adrenal medullary cells have been used in attempts to treat Parkinson's disease, Chronic Pain and to stimulate and promote the survival of other peripheral and CNS neurons. However, the use of adrenal medullary cells to modulate the development of opiate tolerance has not heretofore been attempted. Furthermore, modulation of the development of opiate tolerance by implants of living cells or tissue also has not heretofore been attempted.

SUMMARY OF INVENTION

In accordance with this invention, it has been found that adrenal medullary cells implanted into the CNS can reduce the development of tolerance to opiates. By reducing the development of tolerance to opiates, the implanted cells can thereby inhibit the development of tolerance to, and physical dependence on opiates. The development of morphine tolerance following the continuous use of morphine is significantly reduced in rats with adrenal medullary cell implants compared to rats without such implants.

Thus, it is the principal object of the present invention to establish the ability of adrenal medullary cells to release substances which reduce the development of opiate tolerance without substantial alteration of the analgesic properties of the opiate.

It is a further object of the present invention to provide a method of reducing the development of opiate tolerance by implanting in the central nervous system such cells which release substances to prevent opiate tolerance.

Other objects and advantages will become evident as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1A:
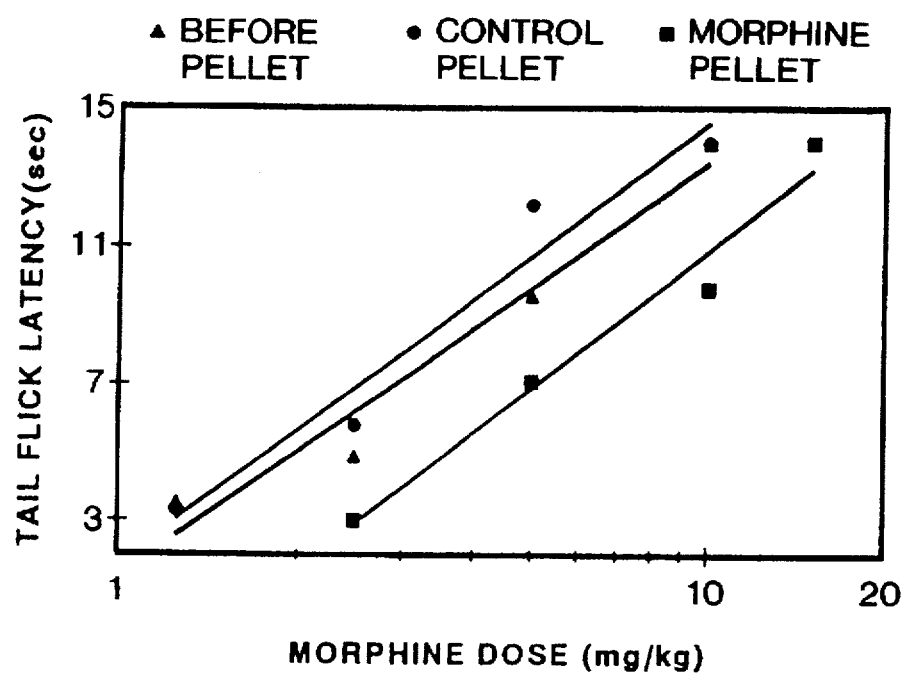
FIGS. 1A and 1B show the dose-response relationships for the effect of morphine assessed by the tail flick test in animals with (A) control transplants and (B) adrenal medullary transplants. The ordinate is the threshold for response to noxious stimuli as assessed by the tail flick test (sec) 20 min following morphine injection. The abscissa represents doses of acute morphine injections (1.25, 2.5, 5, 10 and 15 mg/kg, s.c) plotted on a log scale. Symbols: Triangle, animals before receiving morphine or placebo pellet (n=24); circle, animals 7–9 days following the implantation of a placebo pellet (n=12); square, animals 7–9 days following implantation of a morphine pellet (n=12)

The above and other objects and advantages of the present invention are achieved by a novel method of reducing the development of opiate tolerance by implanting in the central nervous system adrenal medullary cells. Of course, any suitable type of living cells or tissue can be employed so long as such material is transplantable into the CNS without rejection and is capable of releasing effective amounts of substances which reduce the development of opiate tolerance.

It appears that the mechanisms of action of opiate analgesia, tolerance and addiction are separate. Recently, we have generated data that indicates the substances released by adrenal medullary cells modulates opiate tolerance. The data from these studies indicates that implantation of adrenal medullary cells into the CNS before long term courses of opiates, preferably morphine, can reduce the development of tolerance to the analgesic effect of the opiate. The result thereby inhibits the development of tolerance to and physical dependence on opiates. Thus, the implantation of adrenal medullary cells helps maintain responsiveness to future opiate administration.

For the purpose of definition, the term tolerance as used herein is meant to mean a decreased response to a repeated drug dose which requires increasing amounts to produce the same effect. Tolerance is usually manifested by a decreased duration or magnitude of analgesia. Thus, the patient requires larger doses to produce the analgesic effects.

Also for the purpose of definition, the term opiate shall be broadly used to mean a narcotic that is either prepared or derived from opium or is a synthetic narcotic possessing properties characteristic of the opium derived narcotics but not specifically derived from opium.

Unless specifically defined otherwise, all scientific or technical terms used herein have the same meaning as generally understood in the art to which the present invention belongs and all publications mentioned herein are incorporated herein by reference. Although any similar or equivalent methods and materials can be conveniently adopted in the practice or testing of the invention disclosed herein, the preferred methods and materials are now described.

Materials and Methods
Surgical Transplantation Procedure

Adult male Sprague-Dawley rats weighing 300–350 g were used as both donors and recipients. Adrenal medullary tissue was rapidly dissected from the adrenal cortex in ice-cold sterile Hanks' buffer under a dissecting microscope. The tissue was cut into small pieces (less that 0.5 $mm^3$) and medullary tissue from two adrenal glands was transplanted into the spinal cord subarachnoid space of the host animals. Following a laminectomy to expose a 2–3 mm segment of the lumbar enlargement, adrenal medullary tissue was placed into the subarachnoid space through a slit in the dura. Control animals received an equal volume of striated muscle tissue using identical implantation procedures. Following implantation, the musculature was sutured, and the skin closed with wound clips. The animals were returned to their cages, allowed free access to food and water and given a 3 week recovery period after surgery.

Analgesiometric Testing Procedures

To assess changes in responses to noxious stimuli, two analgesiometric tests were used sequentially: the tail flick test and the paw pinch test (Randall-Selitto).

To elicit the tail flick response, a focused beam of high intensity light is applied to the dorsal surface of the rat's tail. The time interval between the onset of the stimulus and the tail flick response is measured at three regions of the tail, the average of which is defined as the "tail flick latency". To prevent tissue damage in the absence of a response, the stimulus is terminated at 14 seconds and the tail flick latency is assigned a value of 14.

The paw pinch response is elicited by a commercially available apparatus (Ugo-Basile) that applies pressure at a constantly increasing rate of 64 g/sec, and automatically terminates at a scale reading of 25 (1000 g). The force is applied to the ventral surface of both hind paws sequentially until the animals react by a withdrawal response.

In all of the following studies, animals were initially screened for baseline pain sensitivities.

EXAMPLE

In order to assess the usefulness of CNS transplants in reducing or preventing opiate tolerance, dose-responsiveness to morphine was assessed in rats with adrenal medullary (n=24) or control muscle (n=24) implants prior to and following the implantation of a morphine pellet. A systemic route of morphine delivery was chosen, as it is the most common route of morphine administration in the clinical setting. Prior to the implantation of the pellets, baseline nociceptive thresholds, and response to morphine sulfate (1.25, 2.5, 5.0, and 10.0 mg/kg, s.c) (n=6 animals per dose) 20 min after injection were assessed using the tail flick and paw pinch tests. Doses higher than 10.0 mg/kg were not used prior to morphine tolerance induction since this dose produced morphine analgesic effects, and higher doses are lethal in some non-tolerant animals.

Morphine pellets (obtained from NIDA) were used to deliver a constant level of morphine and thus providing continuous morphine administration. Pellets were implanted subcutaneously via a small incision in the neck. These pellets contain 75 mg of time-release morphine which is delivered over a two week period. The steady state morphine level attained by these pellets is 105 ng/ml. As a control, placebo pellets of equal size with no morphine were used.

Each group of animals (Adrenal and control transplants) was randomly divided into two subgroups. One subgroup in each group (n=12 for adrenal group, n=12 for control group) received a morphine pellet. The other subgroup (n=12 for adrenal group, n=12 for control group) received a placebo pellet. After a 7–9 day period following pellet implantation, nociceptive responses to acute morphine injections (1.25, 2.5, 5.0, 10.0, 15 mg/kg, s.c.) were again assessed using the method outlined above. In order to allow for six animals in each transplant group to receive each morphine dose, each animal was tested using 2 of the 4 morphine doses (1.25, 2.5, 5.0 and 10.0 mg/kg for animals with adrenal transplant; 2.5, 5.0, 10.0 and 15.0 mg/kg for animals with control transplants). A 1.25 mg/kg dose was not used as 2.5 mg/kg was ineffective in the animals with control transplants due to tolerance. In the adrenal group, the highest dose wasn't used for the same reason as in the pre-pellet trials above.

Statistical analysis was done using two-way analysis of variance (ANOVA) and the Newman-Keuls test for multiple post-hoc comparisons (Keppel et al. Design and Analysis: A Researcher's Handbook, 1973).

FIGS. 1A (tail flick) and 2A (paw pinch) show the dose-response to morphine (1.25, 2.5, 5.0, 10.0 and 15.0 mg/kg) before and after the administration of a 7–9 day continuous dose of morphine in animals which received a control transplant. These results are exactly as expected. While there is no difference in the dose-response curves before and after implantation of placebo pellet (P>0.05), the morphine dose-response curve following chronic morphine administration is shifted to the right (P<0.05). This decrease in antinociceptive responsiveness to various levels of bolus morphine injections is indicative of the development of tolerance.

Figure 1B:
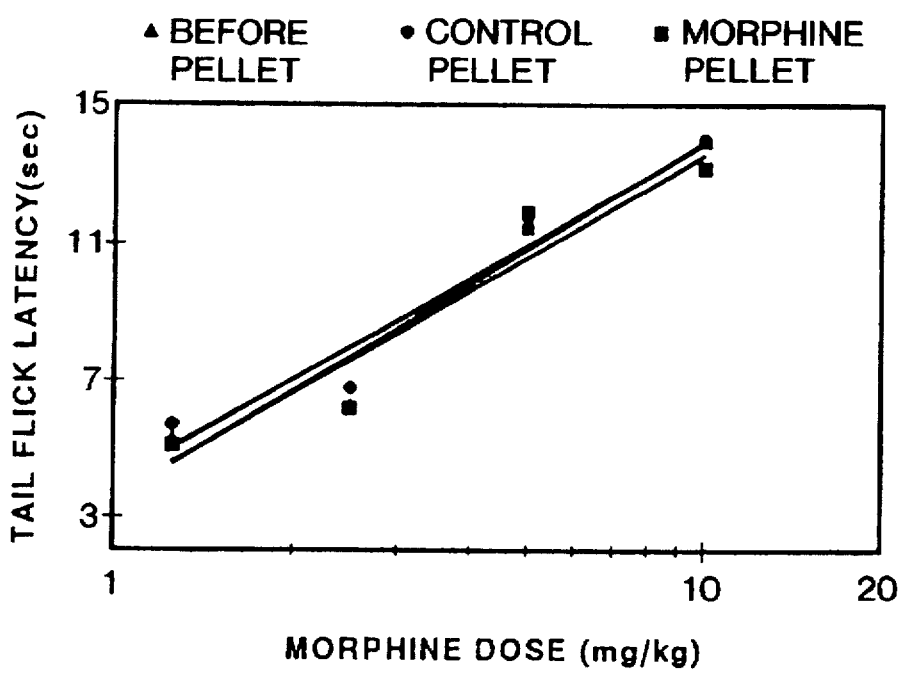
Figure 2A:
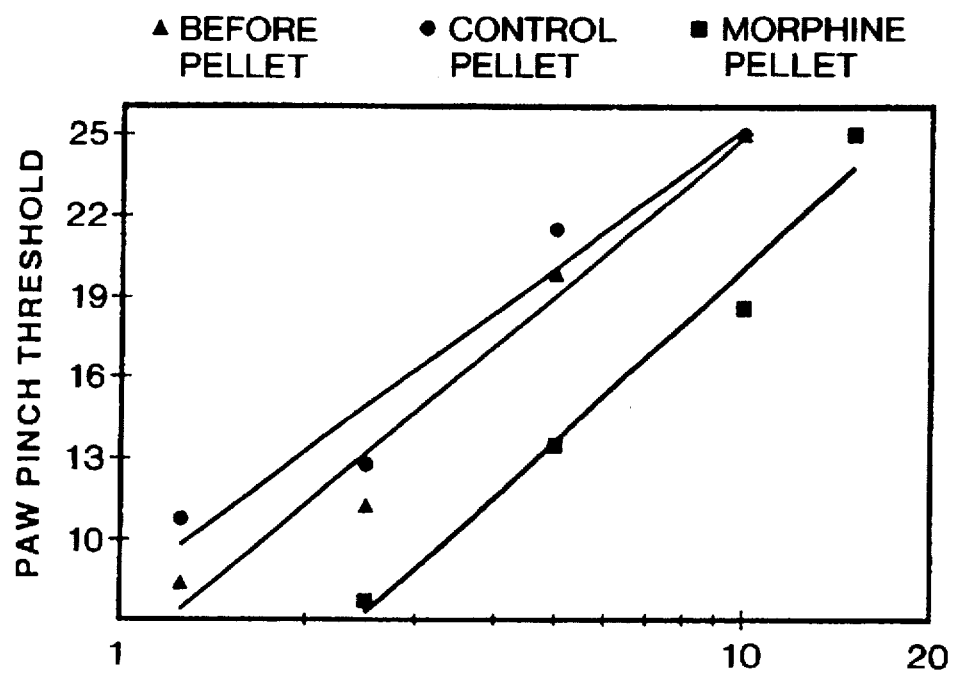
FIGS. 2A and 2B show the dose-response relationships for the effect of morphine assessed by the paw pinch test in animals with (A) control transplants and (B) adrenal medullary transplants. The ordinate is the threshold for response to noxious stimuli as assessed by the paw pinch test 20 min following morphine injection. The abscissa represents doses of acute morphine injections (1.25, 2.5, 5, 10 and 15 mg/kg s.c) plotted on a log scale. Symbols: Triangle, animals before receiving morphine or placebo pellets (n=24); circle, animals 7–9 days following the implantation of a placebo pellet (n=12); square, animals 7–9 days following implantation of a morphine pellet (n=12).
Figure 2B:
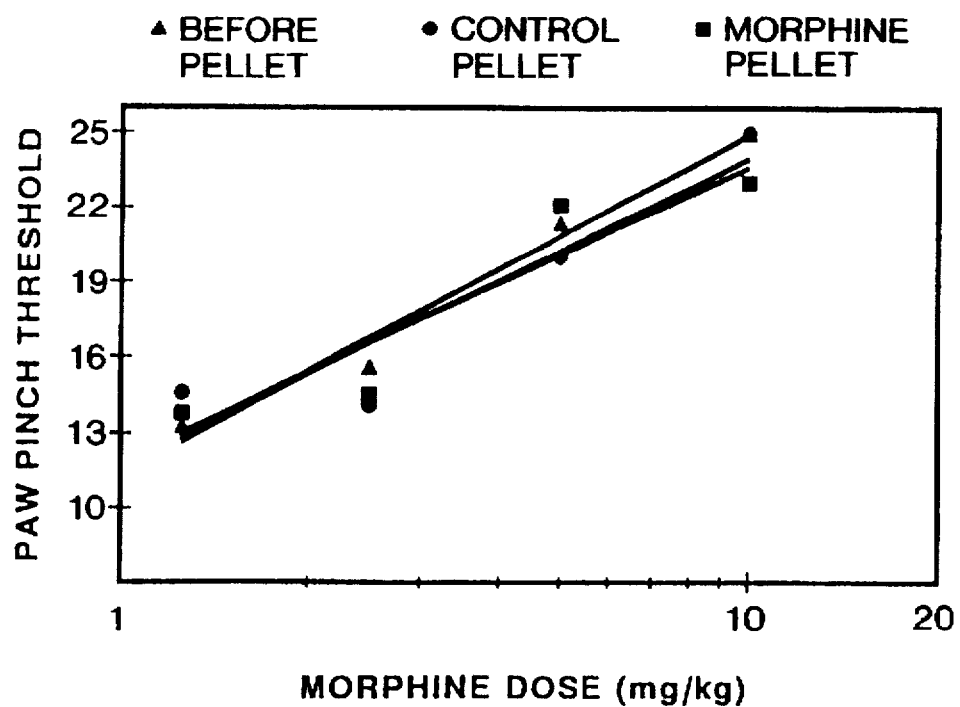

However, FIGS. 1B (tail flick) and 2B (paw pinch) show quite a different result. In the animals which received adrenal medullary transplants, all three dose-response curves (before pellet, after placebo pellet and after morphine pellet) were equivalent ($P>0.05$) establishing the adrenal transplants ability to prevent and/or reduce opiate tolerance development.

Without being bound to one particular theory, it is likely the mechanism of action involves the secretion of substances by the adrenal chromaffin cells into the local CNS. Chromaffin cells have been shown to release substances which have effects on NMDA receptor levels (Hama et al, 1994, Soc. Neurosci. Abstr. Vol 20, part 2, p. 1392) as well as substances which affect NO synthase expression (Hama and Sagen, 1994, Brain Res., 640(1–2):345–51). As noted above, drugs which alter these two physiologic systems have also been shown to have an effect on the development of opiate tolerance.

Whatever the mechanism, the results clearly demonstrate the efficacy of the methods described herein for reducing and/or modulating the development of opiate tolerance. The technique disclosed herein provides a new therapeutic approach for the prevention of opiate tolerance and dependence. Furthermore, because CNS studies on animals can in most cases be transferred to humans, the clinical implications of these results are obvious.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for reducing the development of opiate tolerance in a mammal who will be administered an opiate comprising implanting into a region of the central nervous system of said mammal an effective amount of adrenal chromaffin cells.

2. The method according to claim 1 wherein said region of the central nervous system is the spinal cord.

3. The method according to claim 2 wherein the cells are implanted into the subarachnoid space of the spinal cord.

4. The method according to claim 1 wherein said opiate is morphine.

* * * * *